(12) United States Patent
Jacobs et al.

(10) Patent No.: US 9,615,802 B2
(45) Date of Patent: Apr. 11, 2017

(54) DIRECT CONTROL OF X-RAY FOCAL SPOT MOVEMENT

(71) Applicant: KONINKLIJKE PHILIPS N.V., Eindhoven (NL)

(72) Inventors: Johannes Wilhelmus Maria Jacobs, Boxtel (NL); Frans Henk Kremer, Eindhoven (NL); Heidrun Steinhauser, Ofenpas (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 210 days.

(21) Appl. No.: 14/386,019

(22) PCT Filed: Mar. 8, 2013

(86) PCT No.: PCT/IB2013/051856
§ 371 (c)(1),
(2) Date: Sep. 18, 2014

(87) PCT Pub. No.: WO2013/144752
PCT Pub. Date: Oct. 3, 2013

(65) Prior Publication Data
US 2015/0071405 A1 Mar. 12, 2015

Related U.S. Application Data

(60) Provisional application No. 61/615,430, filed on Mar. 26, 2012.

(51) Int. Cl.
*A61B 6/02* (2006.01)
*A61B 6/00* (2006.01)
*G06F 3/01* (2006.01)

(52) U.S. Cl.
CPC .............. *A61B 6/463* (2013.01); *A61B 6/022* (2013.01); *A61B 6/4007* (2013.01);
(Continued)

(58) Field of Classification Search
CPC .. A61B 6/00; A61B 6/02; A61B 6/022; H04N 13/0221; H04N 13/0203;
(Continued)

(56) References Cited

U.S. PATENT DOCUMENTS 5,065,420 A    11/1991  Levene
6,785,578 B2    8/2004  Johnson et al.
(Continued)

FOREIGN PATENT DOCUMENTS

CN         1464301 A       12/2003
WO      2010051037 A1      5/2010

*Primary Examiner* — Jurie Yun

(57) ABSTRACT

An X-ray imaging system includes an x-ray image acquisition unit, a display unit, an input unit, and adapting means. The x-ray image acquisition unit acquires a first image of a volume of interest of an object in a first projection direction and acquires a second image in a second projection direction. The display unit displays the first and the second image. The input unit determines the second projection direction by an input of a user. The user input includes a change in a viewing-direction of the user viewing the first image. The adapting means adapt a spatial relation between the projection direction of the image acquisition unit and the volume of interest of the object such that the projection direction correlates with the second viewing direction.

14 Claims, 5 Drawing Sheets

(52) U.S. Cl.
CPC ............ *A61B 6/4028* (2013.01); *A61B 6/462* (2013.01); *A61B 6/545* (2013.01); *A61B 6/4441* (2013.01); *G06F 3/011* (2013.01)

(58) Field of Classification Search
CPC ........... H04N 13/0207; H04N 13/0253; H04N 13/0242; H04N 13/0055; G01N 23/00; G01N 23/04; G01N 23/08; G01N 23/083; H05G 1/60
USPC .................................. 378/41, 62, 98.2, 98.5
See application file for complete search history.

(56) References Cited

U.S. PATENT DOCUMENTS

| | | |
|---|---|---|
| 7,538,774 B2 | 5/2009 | Kunita |
| 2003/0007594 A1 | 1/2003 | Ganin |
| 2003/0043966 A1 | 3/2003 | Blin et al. |
| 2007/0083098 A1 | 4/2007 | Stern et al. |
| 2007/0118384 A1 | 5/2007 | Gustafson |
| 2008/0242968 A1 | 10/2008 | Claus et al. |
| 2010/0171822 A1 | 7/2010 | Sawada et al. |

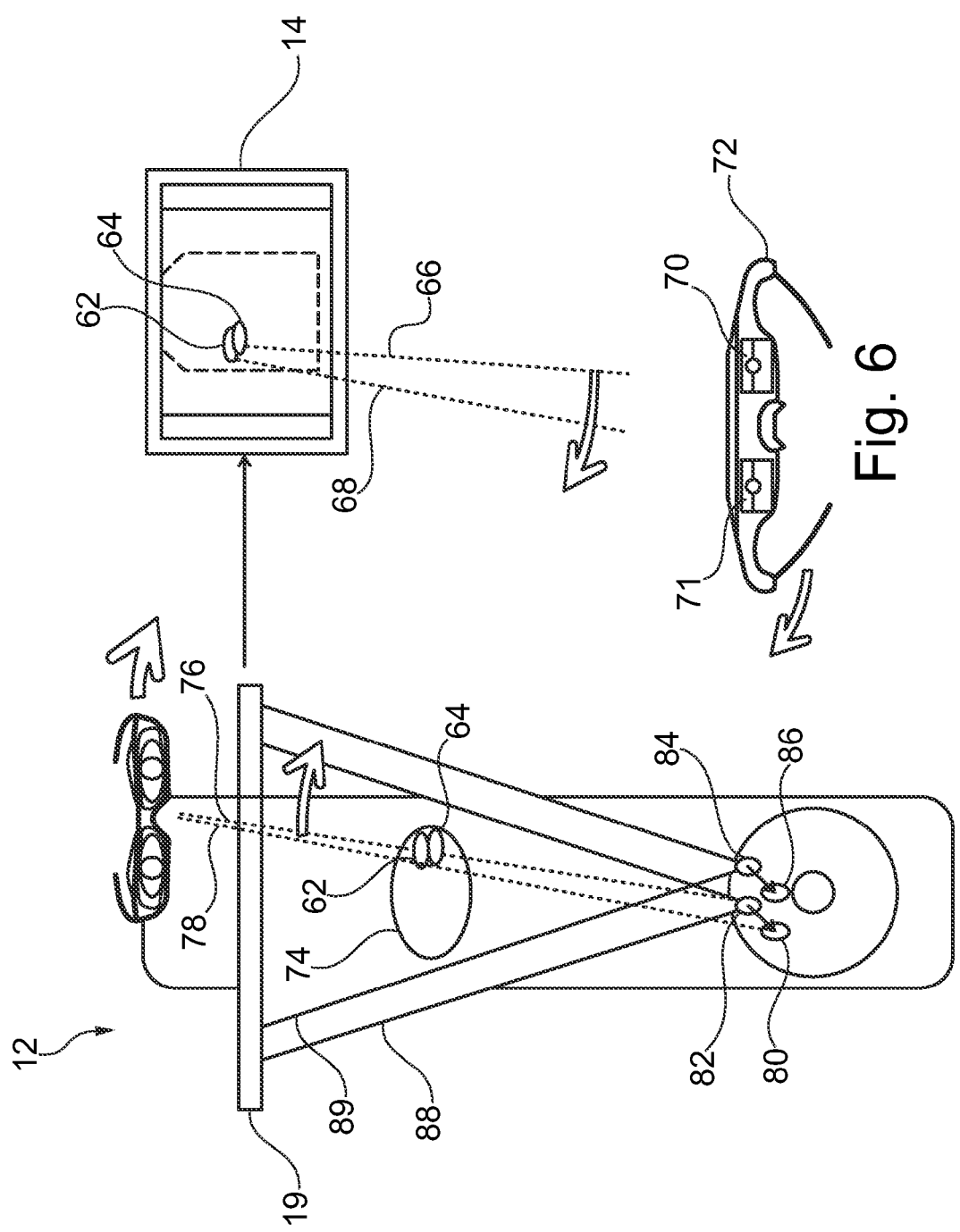

DIRECT CONTROL OF X-RAY FOCAL SPOT MOVEMENT

CROSS REFERENCE TO RELATED APPLICATIONS

This application claims the benefit of International Application Number PCT/IB2013/051856, filed Mar. 8, 2013, and U.S. Provisional Application Ser. No. 61/615,430, filed Mar. 26, 2012, incorporated herein in whole by reference.

FIELD OF THE INVENTION

The present invention relates to providing spatial information of a volume of interest of an object. In particular, the present invention relates to an X-ray imaging system for providing spatial information of a volume of interest of an object, a method for X-ray imaging for providing spatial information of an object, a computer program element, and a computer readable medium.

BACKGROUND OF THE INVENTION

During medical interventions, medical staff is often required to change the projection direction of an imaging system while performing medical actions at the patient, for instance during a surgery. Modern imaging equipment allows to generate images from different directions. In particular, the simultaneous activities of actively controlling an imaging system and performing medical interventions at a patient lead to a certain complexity which the medical staff has to manage. It has been shown that an effective handling of the imaging system by a medical doctor is critical to allow effective workflows during a surgery. US 2003/0043966 describes a radiation emission device and method, wherein the position of a focal point of an anode is dynamically controlled.

SUMMARY OF THE INVENTION

Hence, it can be an object of the present invention to reduce complexity of a workflow in a hospital environment when X-ray imaging is used.

The object of the present invention is solved by the subject-matter of the independent claims, wherein further embodiments are incorporated in the dependent claims.

It should be noted that the following described aspect of the invention also apply for the X-ray imaging system for providing spatial information of a volume of interest of an object, the method, the computer program element, and the computer readable medium.

According to a first aspect of the invention, an X-ray imaging system is provided for providing spatial information of a volume of interest of an object. The X-ray imaging system comprises an image acquisition unit, a display unit, an input unit, and adapting means. The image acquisition unit is configured to acquire a first image of a volume of interest of an object in a first projection direction and to acquire a second image in a second projection direction. The display unit is adapted to display the first and the second image. The input unit is configured for a determination of the second projection direction by an input of a user. The user input comprises a change in a viewing-direction of the user viewing the first image. The adapting means are configured to adapt a spatial relation between the projection direction of the image acquisition unit and the volume of interest of an object such that the projection direction correlates with the second viewing direction.

The term X-ray imaging system describes a system to generate two-dimensional or three-dimensional projections and images using X-ray.

The image acquisition unit is adapted to generate the image comprising an X-ray source, an X-ray detector, and additional mounting or processing means. The image acquisition unit can adapt different projection directions related to a volume of interest, for instance a patient. The volume of interest describes the area or spatial portion of an object, for instance a human body. The two acquired images are supposed to provide different views which can help to capture the spatial dimensions of the examined object. This can be important in particular for certain interventions where it is necessary to navigate a surgical instrument such as a catheter within the human body. The doctor obtains a more realistic impression of the spatial conditions of a particular region within the body.

According to an example it may be necessary to generate images from different spatial directions to calculate a three-dimensional projection. The first image is acquired before the change of the projection direction, the second image is acquired after the change of the projection direction. The change of projection directions may be necessary multiple times during a surgery. Because the change of the imaging direction only requires very simple and intuitive instructions disturbances and distractions are reduced. The ease of use can be significantly increased.

The display unit relates, for instance, to a LCD screen or comparable display devices like projectors that are able to present the image in a two-dimensional or three-dimensional manner. For example in case of a stereoscopic view the display unit presents a pair of images.

Also, 3D glasses which allow a three-dimensional presentation of the image are possible. The described glasses can also comprise small LCD displays positioned directly in front of the user's eyes. This allows to display two different images, each image specifically generated for one particular eye of the user.

According to another example there can be a number of different approaches to 2D/3D viewing:

Normal 2D screens with anaglyphic glasses that can be used to create two views for stereoscopic viewing.

Lenticular (autoscopic) displays with n views and holographic displays allow direct 3D viewing without need for special glasses.

Stereoscopic displays with 2 views use special filter glasses wherein mainly two types are distinguished:
i) active, temporal filtering shutter glasses, and
ii) passive, spatial filtering polarized glasses.
Basically a stereoscopic display shows both views but requires glasses to filter/separate the views for the left and right eye.

Virtual reality glasses which consist of separate (mostly small) screens that display the respective separate images.

The term "input unit" relates to any means that are able to capture a movement or expression of a human being. It allows to translate a human gesture or any human expression into a control signal that can be further processed by the imaging system. Typical human control gestures comprise for instance movement of head, movement of an arm or hand, speech commands, eye movements, and many other gestures. It should be noted that the focus is to use mainly intuitive and natural methods of control, whereas the user input is directly related to or correlated with the displayed image. The input unit can be designed to capture different or various parameters of the user's gesture. This includes the speed of movements, direction of movements, a timely sequence of movements, and others. For instance when viewing a spatial presentation of image, the user would slightly move his head as an intuitive, natural movement to view the examined region from a different angle. The input unit detects that change in position and initiates a change of the imaging direction of the imaging system, in other words, another example is the use of traceable 3D glasses which contain a unit for determining the position of the glasses within a room. Also eye tracking mechanisms are possible which detect a movement of the eye ball or the iris and provide control signals for further processing.

Another input method can also be to move the entire display, for instance to touch a display-like device and turn it into a specific direction. The action of the user can thereby be directly related to the displayed image.

The change in a viewing-direction means that the user changes his position in relation to the image displayed on the display. Adapting means can be any type of mechanical, magnetic, electrical or any other type of means that are able to change the projection direction of the imaging system. Mechanical means can be for instance a movable C-arch, a movable patient table, a movable X-ray source, a movable X-ray detector, or any other type of movable mechanical components. Electrical or electromagnetic adapting means can comprise for instance deflection control means for moving an X-ray focal spot on an X-ray tube anode, or switching between two or more cathodes of an X-ray source. The advantage of electrical or electromagnetic adapting means is that no mechanical movements are necessary which would further disturb the workflow or distract medical staff. In opposite to mechanical movements, electrical adaptation or electromagnetic adaptation performed in much less time. In particular, a focal spot movement has many advantages over a mechanical adaptation in terms of the required time to adjust the projection direction of the imaging system. There can also be combinations of electromagnetic or electrical adjustments and mechanical adaption, for instance a movement of the C-arch is performed simultaneously with a focal spot movement or in a timely sequence. The correlation between the projection direction and the server viewing-direction describes a defined dependency between the two directions. In other words, the change of the projection direction depends on the strength or intensity of the user's input gesture. The advantage of the correlation between the projection direction and the change in viewing-direction is that the user can control the degree of change by the strength or intensity of the user's input gesture. The user input can also be based on voice commands, for instance to start a projection direction change process and a second voice command to stop this process.

According to an exemplary embodiment of the invention, the input unit is a human interface unit configured to detect a movement of the user's head for changing the viewing-direction. Instead of or in addition to turning the head, a moving of the eyes, and/or moving the whole body is provided.

Another example is for instance a hand gesture describing a loop-like movement in the air to control a focal spot movement. A human interface unit is specifically designed for receiving input from human being. The detection of a movement of a user's head can be based on camera-based systems, infrared-based systems, or any kind of positioning systems.

According to an exemplary embodiment of the invention, the input unit is configured to detect a movement of the display activated by the user for changing the viewing-direction. This embodiment describes a scenario where the user moves the display instead of making a gesture by actively moving the display device. The changed position of the display device is detected and translated to control signals. Activating a display can be moving the display, turning for instance a 3D cube, touching a display, or manually turn it.

According to another exemplary embodiment of the invention, the adapting means are configured to at least one of the group of the following:
i) movement of a focal spot of an anode of an X-ray source; and/or
ii) adjustment of a spatial relation between receiving means for receiving the volume of interest and at least an X-ray source of the image acquisition unit.

The term focal spot refers to a spatial region on a surface of an anode of an X-ray tube where the electron beam emitted by the cathode impinges the anode of the X-ray tube. If the focal spot moves to a different position on the anode, the imaging projection direction also changes. The focal spot movement is achieved by deflection means arranged around the electron beam. The advantage of focal spot movements are that they can be performed without any mechanical movements, because they are based on electromagnetic deflection within the X-ray tube. The adjustment of a spatial relation can be based on mechanical movement of the C-arm or other mechanical components of the imaging system. This can be, for instance, movement of a patient table, movement of the entire X-ray source, or moving the detector. The receiving means for receiving the volume of interest may be an object support unit, for example a patient table. The X-ray source comprises all necessary elements to generate X-ray as part of the image acquisition unit.

According to an exemplary embodiment of the invention, the image acquisition unit provides stereo image data, and the first image is a first stereo image and the second image is a second stereo image. Stereo image data contain additional spatial information by combining at least two separate images. This can be obtained by using at least two focal spots within an X-ray source. Stereo 3D imaging can be used to generate three-dimensional images of an object.

According to an exemplary embodiment of the invention, the display unit comprises a first display, configured to present a first image of the stereo image data and a second display configured to present a second image of the stereo image data. The two displays are arranged in relation to the user's eyes such that the first and second images are forming a common viewing-direction towards a virtual point of focus. For the user input, the input unit is configured to detect a movement of the user's head in relation to the common viewing-direction. The first display and the second display can be small displays directly in front of a user's eye as part of a glasses arrangement. This can be typical 3D glasses that contain one display for each eye, wherein for instance the first display is only visible to the left eye and the second display is only visible to the right eye. The two images of the stereo image generated in a way that allows to provide a three-dimensional view to the user. The common viewing-direction towards a virtual point of focus relates to the necessary correlation of the first and the second image to provide a realistic 3D projection. The two displays may be provided as two portions of a common display or display unit.

According to a second aspect of the invention, a method is provided for X-ray imaging for providing spatial information of an object, comprising the following steps:

a) presenting a first image of a volume of interest of an object in a first projection direction;
b) determining a second projection direction based on a user input, wherein the user input comprises changing a viewing direction of the user viewing the first image;
c) adapting a spatial relation between a projection direction of an X-ray imaging system and the volume of interest such that the projection direction correlates with the second viewing direction;
d) acquiring a second image; and
e) presenting the second image.

A volume of interest is a spatial portion of the 3D space extending between the X-ray source and the X-ray detector. The term "projection direction" relates to X-ray generation generated at a focal spot of an anode of an X-ray source towards a detector. The term "correlate" can also include terms like "match", "equal", or "align".

According to an exemplary embodiment of the invention, the user input comprises:

b1) moving the user's head to change the user's viewing direction for viewing the first image; and/or
b2) moving a display presenting the first image to change the user's viewing direction for viewing the first image.

Moving a user's head is a natural intuitive gesture that a user would normally apply when navigating in the three-dimensional space. A gesture can be seen as an intuitive human expression. The user can be a radiologist or medical doctor undertaking a surgical intervention. According to an exemplary embodiment of the invention, the adaptation comprises changing the spatial position of the at least an X-ray source of the X-ray imaging system in relation to the volume of interest.

According to an exemplary embodiment of the invention, the change of the spatial position comprises moving at least one of the group of:

i) the X-ray source;
ii) the X-ray source and a detector of the X-ray imaging system; and
iii) the volume of interest.

The listed movement options can also be provided in any combination.

According to an exemplary embodiment of the invention, the adaptation comprises moving a focal spot location on an anode of an X-ray source.

According to a further aspect of the invention, a computer program element is provided for controlling an apparatus, which, when being executed by the processing unit, is adapted to perform the method.

According to an aspect of the invention, a direct focal spot control mechanism is provided to medical personnel in order to support a flexible adaptation of the imaging system to meet the imaging requirements during a surgery or intervention. During a surgery using X-ray imaging systems, it is required to perform an adaptation and adjustment of components of the imaging systems in a way that it corresponds to workflows executed by medical staff.

In order to directly control the projection direction of an imaging system in relation to, for instance a patient, human gestures and human expressions are translated to control signals to directly adjust the elements of an imaging system. Performing an intervention in a three-dimensional volume requires a view from different angles. While maintaining full focus on the medical intervention, the user can perform simple human expressions to directly influence the projection direction of the imaging system. Whereas moving the C-arm and only mechanical components of the imaging systems is rather slow, the provided movement of the focal spot can be performed without any mechanical movements and can also be combined with said movements of the mechanical elements of the imaging system.

It should be noted that the above features may also be combined. For instance during a focal spot movement the c-arc can turn or shift or there can be a cathode switching simultaneously with a movement of a patient/object table. The combination of the above features may also lead to synergetic effects, even if not explicitly described in detail.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

FIG. 5 schematically shows an imaging system with stereo image acquisition and movement of the focal spots.

FIG. 6 schematically shows a display unit with a first display and a second display.

DETAILED DESCRIPTION OF EMBODIMENTS

Figure 1:
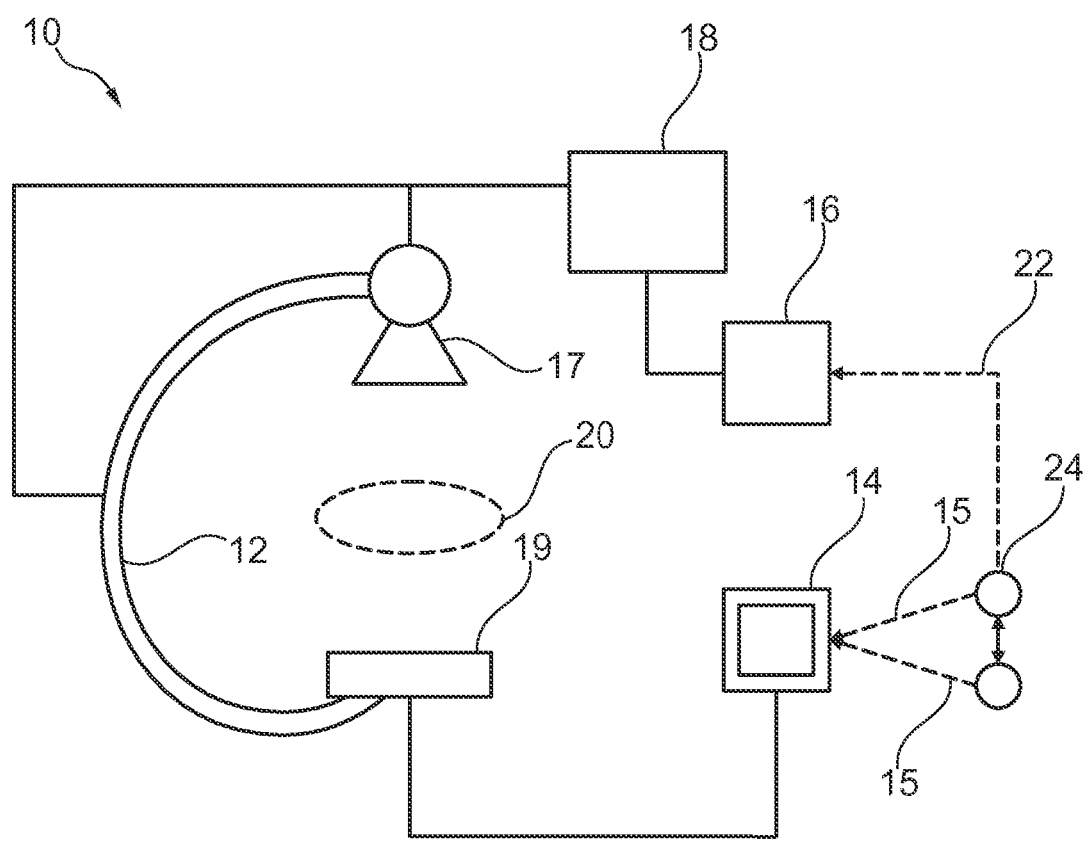
FIG. 1 schematically shows an X-ray imaging system according to an exemplary embodiment of the present invention.

FIG. 1 describes an X-ray imaging system 10 for providing spatial information of a volume of interest 20 of an object. The X-ray imaging system comprises an image acquisition unit 12, adaption means 18, a user input unit 16, a user input signal 22, a user 24, a viewing direction 15 of a user, and a display unit 14. The image acquisition unit 12 comprises an X-ray source 17 and a detector 19, adapted to generate images of a volume of interest 20. The X-ray source 17 emits X-ray radiation which radiates through the volume of interest 20 and is received at the detector 19. The detector 19 and the X-ray source 17 can be mechanically arranged, for instance using a C-arm. The C-arm of the image acquisition unit 12 can be moved in all dimensions of the room. Instead of a C-arm, any other mechanical means can be used. The movement of the different mechanical components of the image acquisition system is achieved by adapting means 18.

The adapting means can be motor-driven means to move parts of the image acquisition system or its elements in terms of their spatial position. Also the adapting means 18 can control the focal spot of the X-ray source 17. This can be instead of or in addition to mechanical movements of parts of the image acquisition system. For adapting the focal spot position in the X-ray source 17, the adapting means can be deflection mechanisms within the X-ray tube to influence the electron beam, in particular direction, shape, energy, or other properties. The volume of interest 20 describes the object that is examined and is located between the X-ray tube and the X-ray detector 19. The adapting means 18 is controlled by the user input unit 16 such that the user input unit generates a control signal transmitted to the adapting means 18. The user input unit 16 is adapted to detect 22 a change of a viewing-direction 15 of a user 24, viewing an image on the display unit 14. The change of the viewing-direction 15 of the user 24 is described with an arrow. The display unit 14 is connected to the detector 19 to receive image data and present the image to the user 24. The change in the viewing-direction 15 of the user 24 can include several gestures or user commands.

Examples are movement of the head, movement of eyes, moving the entire body, turning of the head, describing a loop-like gesture with the hand in the air, or any other intuitive or natural expressions of a user 24. The user input unit 16 is able to translate these input gestures to control signals for the adapting means 18.

Figure 2:
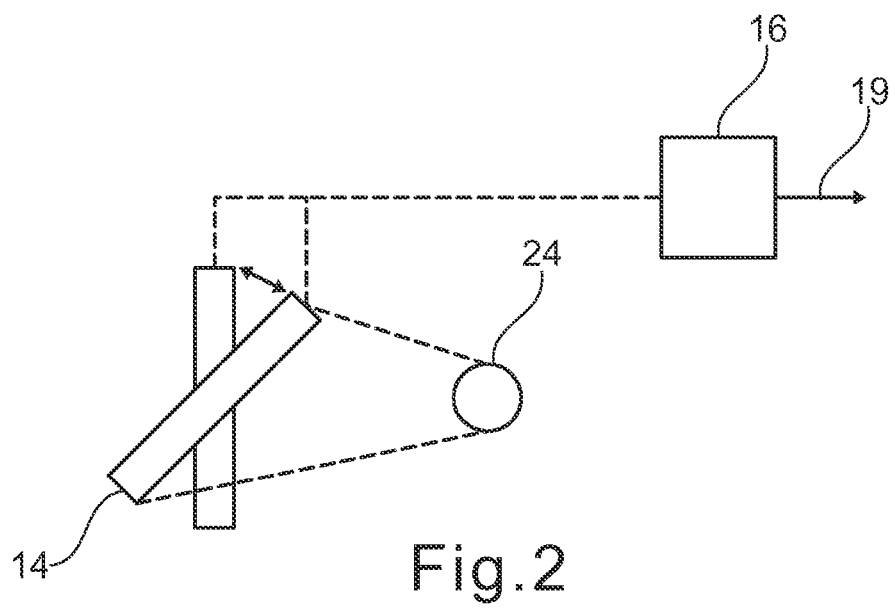
FIG. 2 schematically shows an input unit configured to detect a movement of the display unit by a user.

FIG. 2 describes an input unit adapted to detect a movement of the display unit 14. The unit comprises the display unit 14, the user 24, the user input unit 16, and a control signal 19 to the adapting means. This figure describes an alternative way to change the viewing-direction of a user viewing an image on the display 14. Here, the user actively turns, moves, or changes in any other way the spatial position of the display 14. This movement is detected or measured by the user input unit 16 and translated into a control signal 19. The display can show three-dimensional data to allow the user to obtain a spatial impression of the object. The user 24 can use for instance his hand, a foot, or any other part of the body to directly and mechanically move the display.

Figure 3:
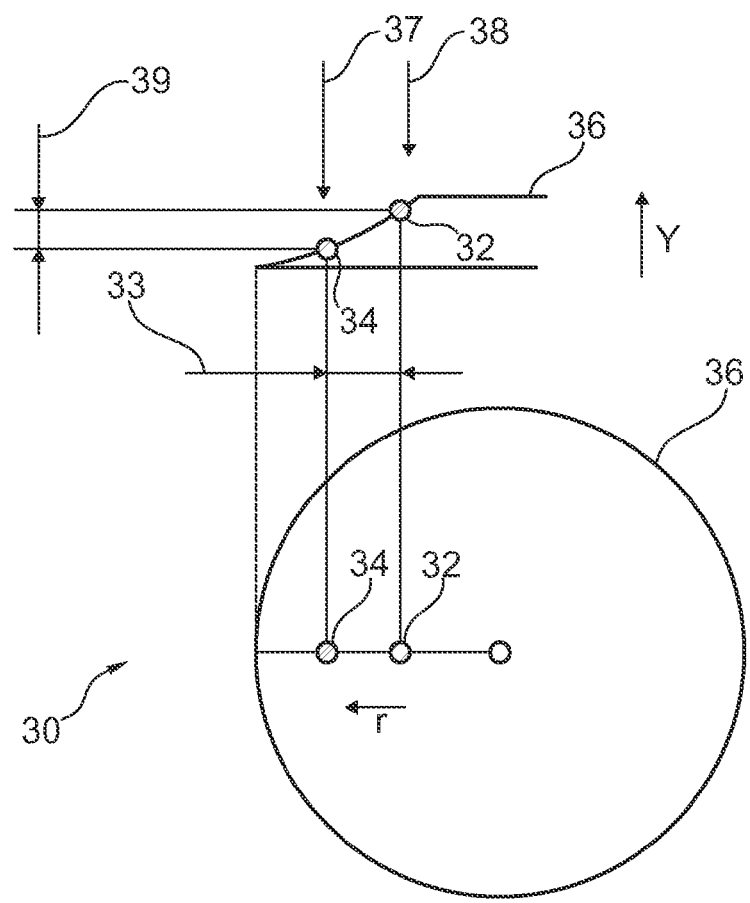
FIG. 3 schematically shows an X-ray source with a moving focal spot.

FIG. 3 shows a movement of a focal spot 32, 34 of an anode 36 of an X-ray source 17. The X-ray source comprises an anode 36, electron beams 37, 38, focal spots 32 and 34, a shift in vertical or y-direction 39, and a shift in a radial r-direction 33. The anode 36 is shown in two different perspectives turned in 90 degrees to each other. The electron beam 38 emitted by the cathode of an X-ray tube is spatially shifted to the position of the electron beam 37. The respective electron beam impinges the anode 36 creating a focal spot which emits X-ray radiation in a radial or "r"-direction. Due to the geometric shape of the anode, the shift of the electron beam and the changed position of the focal spot 32 and 34, also the X-ray radiation emitted by the focal spots shifts accordingly. Given an unchanged position of the volume of interest this shift 39 leads to a change of the imaging projection direction. In other words, a movement or shift of the electron beam leads to a shift or movement of the X-ray, changing the projection direction. It should be noted that there can be many different embodiments of the anode in terms of shape, material, and other characteristics that may influence the focal spot and the respective shifts.

Figure 4:
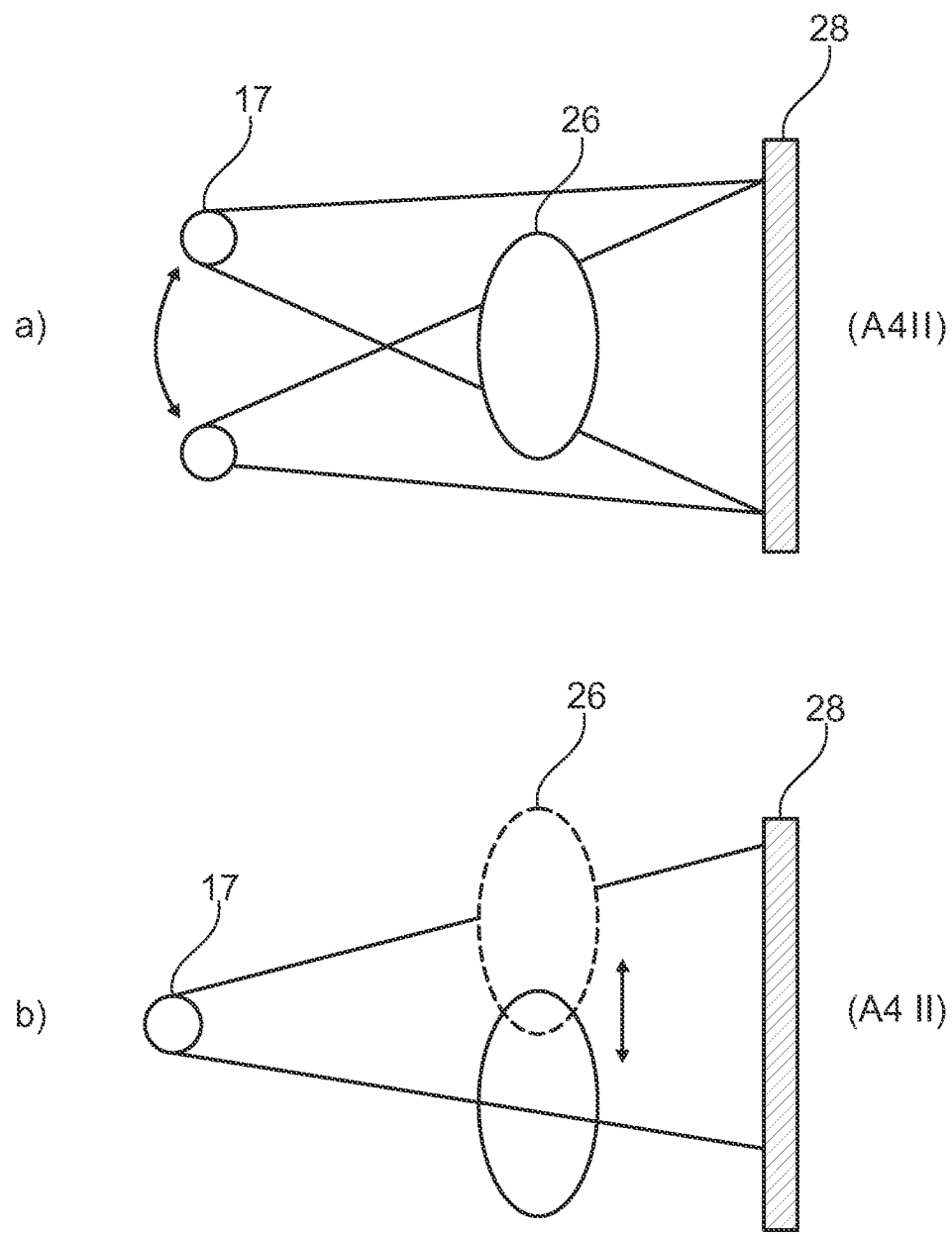
FIG. 4 schematically shows two options of adjustment of a spatial relation between receiving means for receiving the volume of interest, and an X-ray source of the image acquisition unit.

FIG. 4 illustrates two options of an adjustment of a spatial relation between receiving means for receiving the volume of interest 26, and at least one X-ray source 17 of an image acquisition unit. A first option is to change the position of the X-ray source 17 and maintain the position of the volume of interest and the detector. The movement of the X-ray source 17 is indicated with the arrow in option A. In opposite to the first option, the FIG. B describes a movement of the volume of interest 26, wherein the position of the X-ray source 17 and the detector 28 is not changed. The movement of the X-ray source 17 can be achieved for instance by switching between two or more X-ray tubes mounted on different spatial positions of the imaging system, or mechanical movement of an X-ray tube, movably mounted on the image acquisition unit.

In FIG. 5, an image acquisition system is described that is able to generate stereo images. The stereo image acquisition unit 12 comprises a stereo focal spot with a first focal spot 82 and a second focal spot 84 for generation of a first stereo image. Applying the previously described focal spot movement, a new pair of focal spots 80 and 86 is provided to generate a second stereo image. Each focal spot generates a beam of X-ray radiation such that the first focal spot 82 generates a first X-ray beam 88 towards the X-ray detector 14. The second focal spot 84 accordingly generates a corresponding X-ray beam 89 towards the same detector 19. If the pair of focal spots are moved from their first positions 82/84 to their new positions 80/86, the respective X-ray beams 88 and 89 also move accordingly. In this figure, the X-ray beams 88 and 89 are only shown for the first position of the dual focal spots 82 and 84.

Furthermore, the image acquisition unit 12 further comprises a volume of interest 74, a first object 62, and a second object 64. One objective of the imaging procedure can be to clearly separate the two objects 62 and 64 in a displayed image 14. The displayed image 14 is also referred to as display unit 14 or display 14. In the shown case, the object 62 is not clearly visible in the image, because it is located spatially behind the second object 64. In order to make the object 62 visible to the physician, the projection direction towards the two objects 62 and 64 is changed through focal spot movement. The first imaging projection direction is shown as line 78, and the second imaging projection direction after moving the focal spots is indicated with the line 76. The advantage is that through the change of the imaging projection direction, now the object 62 becomes at least better or more visible.

According to another embodiment of the invention a further aspect is addressed: In 2D X-ray images it can sometimes be difficult to determine which object out of two visible overlaying objects is in front and which one is behind the respective other object. Stereoscopic 3D viewing can help to distinguish. However, if the objects overlap too much it might still be difficult, especially when the overlapping images are blood vessels both parallel to the stereo vision. A slight change of the imaging projection direction according to the present invention, for instance a movement of the focal spot, in order to generate a second view can help to better distinguish. Also the position of objects in the 3D space and their spatial relation to each other can be better identified.

According to another embodiment of the invention during stereoscopic viewing a slight change of the imaging projection pairs (left and right view in stereoscopic viewing) can help to better distinguish the objects.

For the presentation of the image, the system further comprises a display unit 14 displaying the objects 62 and 64. The black lines 68 and 66 describe a first and a second viewing-direction of the physician viewing the image on the display 14. In this figure, the physician changes his viewing-direction from a first or initial viewing-direction 66 to a second viewing-direction 68 by performing one of the above described gestures or input commands. The display 14 can be capable to display stereo image information in a three-dimensional manner. By changing the viewing-direction, the physician initiates a change of the imaging projection direction of the image acquisition unit. For example, in order to better see the second object 62, the physician slightly turns his head, which is translated into control signals that change the focal spot position from the first focal spot locations 82/84 to the second focal spot locations 80/86, which leads to a change of the projection direction which then triggers the generation of a next image shown on the display 14.

FIG. 6 shows an example of a display arrangement 72 comprising a first display 71 and a second display 70. The displays 70 and 71 are arranged such that each display can present one image out of a stereo image and in a way that both images are forming a common viewing-direction towards a virtual point of focus. For example, the given 3D glasses arrangement can present a first image of a stereo image to a first eye and can present a second image out of a stereo image to a second eye. The advantage is that this way, the user can see a three-dimensional view of the object of interest. This shown arrangement can further comprise a positioning unit that allows the determination of a spatial position to detect movements for instance of the head.

The display can also comprise an arrangement of a first 3D display and/or corresponding 3D glasses belonging to the 3D display. This can be for instance active shutter glasses or passive polarized glasses. In this example, FIG. 6 can be seen as part of the system shown in FIG. 7 describing an embodiment where the display includes both a 3D capable display or screen and suitable 3D glasses to be worn by the user.

Figure 7:
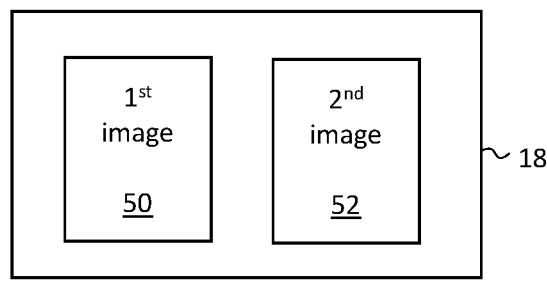
FIG. 7 schematically shows a stereo image data comprising a first image and a second image.

FIG. 7 shows stereo image data 18 comprising a first image 50 and a second image 52.

Figure 8:
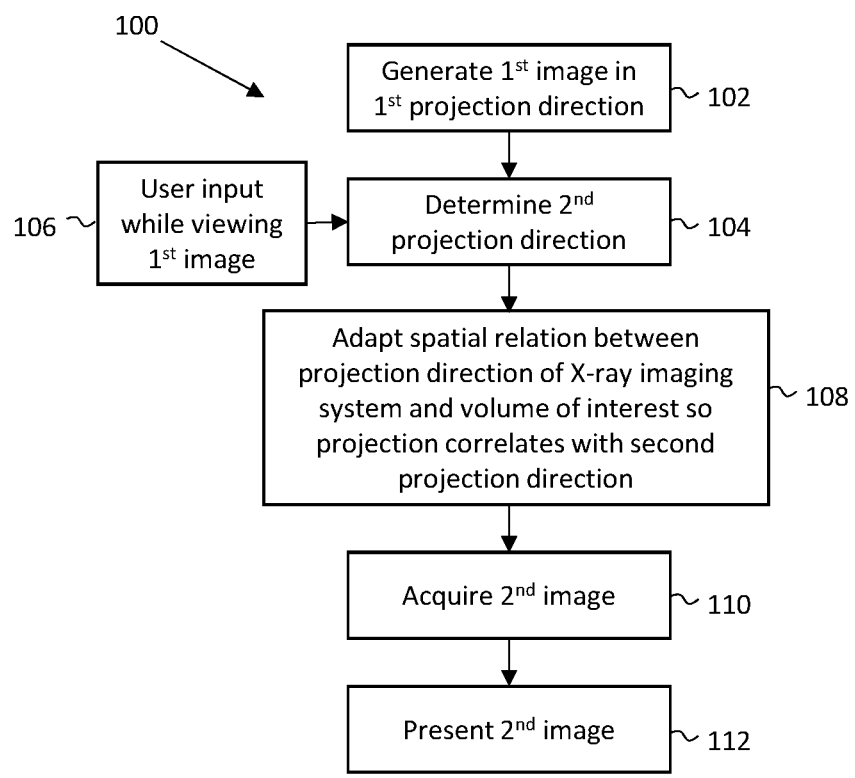
FIG. 8 describes a method for providing spatial information of an object.

FIG. 8 describes a method 100 for X-ray imaging for providing spatial information of an object. In a first step 102, a first image of a volume of interest of an object is generated in a first projection direction. The image is created using for instance an X-ray imaging system. In a second step 104, a second projection direction is determined. This determination is based on a user input 106 which comprises a change of the user's viewing-direction when viewing the first image. In a further step 108, a spatial relation is adapted between a projection direction of the X-ray imaging system and the volume of interest, such that the projection direction correlates with the second viewing direction. The user input can be based on a movement of the user's head or various gestures, but also by moving the display presenting the first image. Step 108 describes the adaption of a spatial relation between a projection direction of an X-ray imaging system and the volume of interest, such that the projection direction correlates with the second viewing-direction. The adaptation can be performed either based on mechanical adaptations using mechanical components of the image acquisition system, such as a C-arch movement, movement of a patient table, or moving the focal spots on the anode of an X-ray source. In the following step 110, a second image is acquired. The last step 112 describes the presentation of the second image. This presentation can be performed by the display unit presenting the image to the user.

The first step 102 is also referred to as step a), the second step 104 as step b), the third step 108 as step c), the fourth step 110 as step d) and the last step 112 as step e). An example of this method can be that a physician undertaking a intervention views a first image that is presented on an LCD screen. In order to better see a second object in a region of the patients body he slightly turns his head into the target direction. This change of the doctors viewing direction is detected and processed in the imaging system. The adapting means are now used to change the projection direction of the x-ray source/detector arrangement in relation to the examined region of the patients body. The c-arm moves to a new position and the focal spot of the x-ray tube changes his position on the anode. The degree of changes correlate to the movement of the doctor's head. Then a second image is generated and displayed on the LCD screen.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system comprising:
   an X-ray image acquisition unit,
   a display unit,
   an input unit, and
   adapting means; wherein:
   the X-ray image acquisition unit acquires a first stereo image of a volume of interest of an object in a first projection direction and acquires a second stereo image of the volume of interest in a second projection direction;
   the display unit displays the first stereo image and the second stereo image;
   the display unit comprises a first display device that displays first stereoscopic imagery and a second display device that displays second stereoscopic imagery;
   the first and second display devices are arranged in relation to a user's eyes such that the first and second stereoscopic imagery are formed, for the user, in a common viewing direction towards a virtual point of focus;
   the input unit determines the second projection direction from an input of the user;
   the user input indicates a change in a viewing direction of the user viewing the first stereo image; and
   the adapting means adapt a spatial relation between the projection direction of the image acquisition unit and the volume of interest of the object such that the second projection direction correlates with the change in the viewing direction.

2. The X-ray imaging system according to claim 1, wherein the input unit is a human interface unit configured to detect a movement of the user's head for changing the viewing direction.

3. The X-ray imaging system according to claim 1, wherein the input unit is configured to detect a movement of the display unit activated by the user for changing the viewing direction.

4. The X-ray imaging system according to claim 1, wherein the adapting means:
   i) move a focal spot of an anode of an X-ray source of the image acquisition unit; or
   ii) adjust a spatial relation between receiving means for receiving the volume of interest and the X-ray source.

5. The X-ray imaging system according to claim 1, further comprising a processing unit, which comprises a computer program element for controlling the X-ray imaging system.

6. A non-transitory computer readable medium having stored the program element of claim 5.

7. The X-ray imaging system according to claim 1, wherein the adapting means comprise a movable C-arch, a movable patient table, a movable X-ray source, or a movable X-ray detector.

8. The X-ray imaging system according to claim 1, wherein the adapting means comprise a deflection control means for moving an X-ray focal spot on an X-ray tube anode or means to switch between two or more cathodes of an X-ray source.

9. The X-ray imaging system according to claim 1, wherein the display unit comprises:
   anaglyphic glasses that create two views for stereoscopic viewing,
   lenticular displays with two views,
   holographic displays that provide direct 3D viewing,
   stereoscopic displays with two views comprising active, temporal filtering shutter glasses or passive, spatial filtering polarized glasses, or
   virtual reality glasses comprising a separate screen for displaying each of the first and second first and second stereoscopic imagery.

10. A method for X-ray imaging, the method comprising:
    a) acquiring, with an X-ray imaging system, a first stereo image of a volume of interest of an object and displaying, on a display device, the first stereo image in a first projection direction;
    b) determining a second projection direction based on a user input; wherein the user input identifies a change of viewing direction of the user viewing the first stereo image;
    c) adapting a spatial relation between a projection direction of the X-ray imaging system and the volume of interest such that the second projection direction correlates with the change of the viewing direction;
    d) acquiring, with the X-ray imaging system, a second stereo image in the second projection direction; and
    e) displaying, on the display device, the second stereo image; wherein
    the display of each of the first and second stereo images is arranged in relation to the user's eyes so as to form a common viewing direction towards a virtual point of focus.

11. The method of claim 10, wherein the user input identifies the change of viewing direction based upon:
    b1) a movement of the user's head or
    b2) a movement of the display device.

12. The method of claim 10, wherein the adaptation in step c) comprises changing the spatial position of an X-ray source of the X-ray imaging system in relation to the volume of interest.

13. The method of claim 12, wherein the change of the spatial position comprises moving:
    the X-ray source;
    the X-ray source and a detector of the X-ray imaging system; or
    the volume of interest.

14. The method of claim 10, wherein the adaptation in step c) comprises moving a focal spot location on an anode of an X-ray source.

* * * * *